(12) United States Patent
Moten

(10) Patent No.: US 11,951,033 B2
(45) Date of Patent: Apr. 9, 2024

(54) CONTRACEPTIVE UNDERGARMENT

(71) Applicant: Candice Moten, Fort Worth, TX (US)

(72) Inventor: Candice Moten, Fort Worth, TX (US)

(*) Notice: Subject to any disclaimer, the term of this patent is extended or adjusted under 35 U.S.C. 154(b) by 315 days.

(21) Appl. No.: 17/471,091

(22) Filed: Sep. 9, 2021

(65) Prior Publication Data
US 2022/0071799 A1 Mar. 10, 2022

Related U.S. Application Data
(60) Provisional application No. 63/076,073, filed on Sep. 9, 2020.

(51) Int. Cl.
- *A61F 6/04* (2006.01)
- *A41B 9/02* (2006.01)
- *A61F 6/06* (2006.01)

(52) U.S. Cl.
CPC ............... *A61F 6/04* (2013.01); *A41B 9/023* (2013.01); *A61F 2006/041* (2013.01)

(58) Field of Classification Search
CPC ............ A61F 6/04; A61F 2006/041; A61F 2006/047; A61F 6/06; A41B 9/023; A41B 9/12; A41B 9/026; A41B 9/002; A41B 9/001; A41B 1/065; A41B 9/02; A41D 1/065
See application file for complete search history.

(56) References Cited

U.S. PATENT DOCUMENTS

| | | | | |
|---|---|---|---|---|
| 4,807,611 A * | 2/1989 | Johnson | ............... | A61F 6/065 604/349 |
| 4,862,901 A * | 9/1989 | Green | ............... | A61F 6/065 604/347 |
| 4,966,165 A * | 10/1990 | Anderson | ............... | A61F 6/065 128/830 |
| 5,181,527 A * | 1/1993 | Dorsey | ............... | A61F 6/065 128/830 |
| 5,209,241 A * | 5/1993 | Hardy | ............... | A61F 6/065 128/842 |
| 5,269,320 A * | 12/1993 | Hunnicutt | ............... | A61F 6/065 604/347 |
| 5,535,757 A * | 7/1996 | Fleming, Jr. | ............... | A61F 6/04 128/842 |
| 5,638,829 A * | 6/1997 | Najor | ............... | A61F 6/065 128/842 |
| 5,687,741 A * | 11/1997 | Torger | ............... | A61F 6/065 128/842 |
| 6,035,853 A * | 3/2000 | Alla | ............... | A61F 6/06 128/830 |

* cited by examiner

*Primary Examiner* — Camtu T Nguyen
(74) *Attorney, Agent, or Firm* — Brennan, Manna & Diamond, LLC

(57) ABSTRACT

The present invention relates to a contraceptive undergarment. The contraceptive undergarment is designed to be used by both males and females and can be constructed in variants adapted for the male anatomy, the female anatomy, for more coverage area and for anal penetration. The undergarment for the male anatomy includes an integrated penis cover or condom cover. The undergarment for anal penetration includes a thinner layer of latex at the central buttock line. The contraceptive undergarment, in one embodiment, is made up of latex and prevents skin-on-skin contact and forms a barrier between two partners to avoid transmission of sexually transmitted diseases, and exchange of bodily fluids, while maintaining sexual pleasure.

7 Claims, 4 Drawing Sheets

CONTRACEPTIVE UNDERGARMENT

CROSS-REFERENCE TO RELATED APPLICATION

The present application claims priority to, and the benefit of U.S. Provisional Application No. 63/076,073, which was filed on Sep. 9, 2020 and is incorporated herein by reference in its entirety.

FIELD OF THE INVENTION

The present invention relates generally to the field of contraception garments. More specifically, the present invention relates to a contraceptive undergarment for both males and females and can be in the form of a unisex short or long boxer, a female undergarment and a male garment. The male undergarment includes an integrated penis cover for receiving a penis of a male wearer. The contraceptive undergarment includes a waistband, a pair of leg openings and can comprise latex or a similar material with which a condom is generally made. More specifically, the different varieties of the contraceptive undergarment include one for the male anatomy, one for the female anatomy, one with more coverage area and another for anal penetration. The contraceptive undergarment prevents skin on skin contact, and forms a barrier between two partners. Accordingly, the present disclosure makes specific reference thereto. Nonetheless, it is to be appreciated that aspects of the present invention are also equally applicable to other like applications, devices, and methods of manufacture.

BACKGROUND OF THE INVENTION

By way of background, individuals try to avoid use of condoms and other physical contraception during sexual intercourse as they can decrease the sexual pleasure for the partners. However, sexually-transmitted diseases (STDs) can occur without the use of contraception during sexual intercourse. Not using contraception may end up in unwanted pregnancies. Additionally, individuals may end up taking oral pills afterwards, which can be harmful over time.

Further, the condoms and other physical barriers provide limited protection from STDs. Body fluids end up being exchanged to some level during sexual intercourse, which can lead to STD transmission and may also result in unwanted pregnancies.

The most annoying difficulty in conventional physical contraception is that individuals need to remove their undergarments, unwrap contraception packages, apply, fit, and use the contraception. Many present contraception devices cause discomfort or lead to loss of pleasure for the user.

Generally, undergarments are items of clothing worn beneath outer clothes, usually in direct contact with the skin, although they may comprise more than a single layer. Undergarments serve to keep outer garments from being soiled or damaged by bodily excretions, to lessen the friction of outerwear against the skin, to shape the body and to provide concealment or support for parts of the anatomy. Individuals desire an undergarment be made available that can be worn while performing sexual intercourse without compromising safety, pleasure and disease prevention.

Therefore, there exists a long felt need in the art for an improved contraception undergarment that allows individuals to maintain pleasure and that does not cause discomfort. There is also a long felt need in the art for an improved means of contraception that prevents transmission of sexually-transmitted diseases. Additionally, there is a long felt need in the art for an improved contraception method that prevents unintentional pregnancies. Moreover, there is a long felt need in the art for an improved contraception device that can be worn like an undergarment while performing sexual intercourse. Further, there is a long felt need in the art for an improved form of contraception that accommodates both male and female anatomies. Finally, there is a long felt need in the art for an improved contraception undergarment that allows individuals to maintain comfort while offering a safe contraceptive method.

The subject matter disclosed and claimed herein, in one embodiment thereof, comprises a contraceptive undergarment. The contraceptive undergarment further comprises: a frontal region to cover a front portion of a wearer; a rear region to cover the buttocks of the wearer; a pair of leg openings to insert the legs of the wearer therethrough; a waistband to create an opening to receive and encircle the waist of the wearer; a penis cover integrally-connected to the frontal region, wherein the penis cover is in a condom shape and is configured to cover the entire length or a partial length of the penis; the penis cover includes an opening in the frontal region to insert a penis into the penis cover, wherein the penis cover allows the penis to move freely during sexual intercourse while preventing exchange of body fluids to prevent pregnancy, transmission of sexually-transmitted diseases and other infections. In other embodiments of the contraceptive undergarment, the penis cover is not present, and the undergarment can be used by both male and female wearers.

In this manner, the novel contraceptive undergarment of the present invention accomplishes all of the foregoing objectives and provides a relatively safe and convenient undergarment to allow sexual partners to have safe intercourse while maintaining desired safety prohibitions to avoid exchange of body fluids, such as sperm and vaginal discharge. The contraceptive undergarment maintains comfort for both partners throughout intercourse, while eliminating the need to use additional contraception.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a contraceptive undergarment. The contraceptive undergarment further comprises: a frontal region to cover a front portion of a wearer; a rear region to cover the buttocks of the wearer; a pair of leg openings to insert the legs of the wearer; a waistband to create an opening to receive and encircle the waist of the wearer; a penis cover integrally-connected to the frontal region wherein the penis cover is in a condom shape and is configured to cover the entire length or a partial length of the penis; the penis cover includes an opening in the frontal region to insert the penis into the penis cover, wherein the penis cover allows the penis to move freely during sexual intercourse, while preventing exchange of body fluids to prevent pregnancy, transmission of sexually transmitted diseases and other infections.

In yet another embodiment of the present invention, a contraceptive undergarment comprises one or more materials of latex, polyurethane, polyisoprene and lambskin. The penis cover can have a layer or coating of a flavoring agent and spermicidal.

In yet another embodiment of the present invention, a short boxer contraceptive undergarment for anal sex and vaginal sex is disclosed. The short boxer contraceptive undergarment is made up of latex or similar material, and includes a pair of leg openings, a waistband to create an opening to receive and encircle the waist of the wearer, a thinner layer of latex near the central buttock line and near the crotch area, allowing safe, secure and easy anal sex and vaginal sex while wearing the undergarment.

In yet another embodiment of the present invention, the contraceptive undergarment can be in the form of a unisex long boxer made up of one or more of latex, polyurethane, polyisoprene and lambskin.

In yet another embodiment of the present invention, a female contraceptive undergarment is disclosed. The female contraceptive undergarment can be in the shape of a female panty or similar, and is designed to be used for protection during sexual intercourse. The female undergarment includes two leg openings and a crotch area between the leg openings that can be used as a protective measure to prevent the exchange of bodily fluids while allowing sexual intercourse. The crotch area can be pushed inside a vagina of a female while performing intercourse, thereby acting as a barrier between skin to skin contact of the female and the other sexual partner.

In yet another embodiment, a sanitary pad can be placed inside the crotch area of the female underwear when not in use for sexual intercourse. The material of the undergarment can be latex or similar, and can be breathable and stretchable.

In yet another embodiment, a method for donning a contraceptive undergarment is described. The method includes providing the contraceptive undergarment, inserting limbs into the leg openings of the contraceptive undergarment, pulling up the contraceptive undergarment easily by grasping the waistband for a firm and secure grip and covering the genital and buttocks areas of the wearer. When the garment is worn over the body, the undergarment provides contraceptive protection, et. al., while performing sexual intercourse.

In a further embodiment of the present invention, the contraceptive undergarment of the present invention allows individuals to engage in safe and secure intercourse while maintaining sexual pleasure. The undergarment creates a barrier from skin on skin contact between individuals to prevent the spread of disease, while maintaining comfort and offering a safe contraceptive method. The undergarment can come in a variety of designs and sizes, and can be constructed to conform to both male and female anatomies.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1A:
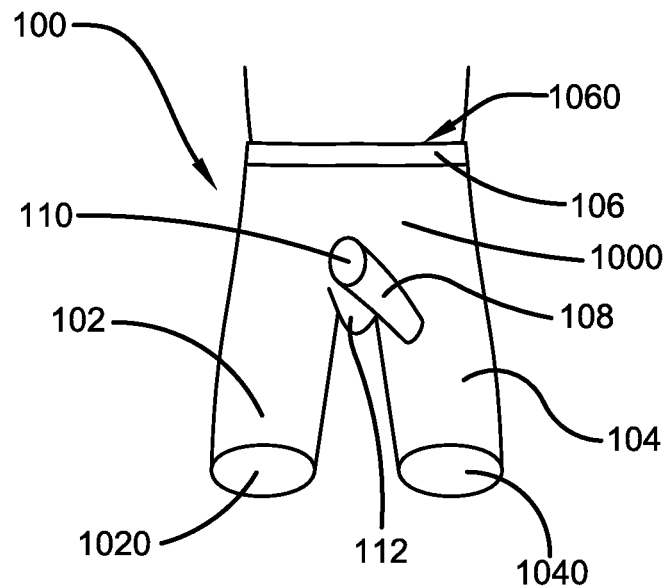
FIG. 1A illustrates a front perspective view of one potential embodiment of contraceptive underwear of the present invention designed for a male user in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long felt need in the art for an improved contraception undergarment that allows individuals to maintain pleasure and that does not cause discomfort. There is also a long felt need in the art for an improved contraception undergarment that prevents transmission of sexually transmitted diseases. Additionally, there is a long felt need in the art for an improved contraception undergarment that prevents unintentional pregnancies. Moreover, there is a long felt need in the art for an improved contraception undergarment that can be worn like a regular undergarment while performing sexual intercourse. Further, there is a long felt need in the art for an improved contraception undergarment that accommodates both male and female anatomies. Finally, there is a long felt need in the art for an improved contraception undergarment that allows individuals to maintain comfort while offering a safe contraceptive method.

The present invention, in one exemplary embodiment, is a unisex short boxer contraceptive undergarment for anal sex and vaginal sex. The short boxer contraceptive undergarment is made up of latex or similar, and includes a pair of leg openings, a waistband to create an opening to receive and encircle the waist of the wearer, a thinner layer of latex near the central buttock line and near the crotch area, thereby allowing safe, secure and easy anal sex and vaginal sex while wearing the undergarment.

Referring initially to the drawings, FIG. 1A illustrates a front perspective view of one potential embodiment of contraceptive underwear of the present invention designed for a male user in accordance with the disclosed architecture. The contraceptive male underwear 100 is designed like a conventional boxer and is to be worn like conventional underwear by a male during sexual intercourse. The male underwear 100, in one exemplary construction, can be made of soft latex, the same material as a condom. More specifically, the contraceptive male underwear 100 includes a frontal region 1000 to cover a front portion of a wearer and a rear region (shown as 120 in FIG. 1B) to cover the buttocks of the wearer. A right leg element 102 with a right leg opening 1020 and a left leg element 104 with a left leg opening 1040. The leg openings 1020, 1040 are used for inserting the legs of a male wearer for wearing the male contraceptive underwear 100. The male underwear 100 includes a waistband 106 defining a waist opening 1060 to receive and encircle the waist or abdomen of a wearer. The waistband 106 can be soft and elastic.

The male underwear 100 includes a penis cover 108 extending from an opening 110. The penis cover 108 is elastic, soft, and is configured to receive the penis of a male wearer of the underwear 100. When worn by a male user, the penis cover 108 prevents the penis of the wearer from touching the skin of an intercourse partner and thus prevents the exchange of bodily fluids. The penis cover 108 acts like a condom for the male wearer, and prevents unwanted pregnancies and transmission of sexually transmitted diseases. For providing additional comfort to the wearer, the underwear 100 includes a scrotum bag 112 to receive and stabilize the scrotum of the male user during sexual intercourse. The scrotum bag 112 also reduces the pressure on the testicles during intercourse, and can be made up of latex or similar.

The penis cover 108 comes in a variety of sizes, thereby allowing the users to choose as per their preferences and can conform to the shape of a male penis and especially to the shape of the glans. The cover 108 is soft to the foreskin of the penis and does not cause discomfort or lead to loss of pleasure during sexual intercourse. The penis cover 108 allows the penis to lean downward towards the scrotum, and also allows the penis to lean to predetermined angles or greater in the left, right, or upward direction. The penis cover 108 keeps the male reproductive organ in a dry, breathable and radiating natural normal and excited state.

The advantage of the contraceptive male underwear 100 is that it can be worn easily and comfortably under the trousers or even under conventional underwear, shorts or boxers. For users that are allergic to latex, the contraceptive male underwear 100 can be constructed of one or more of polyurethane, polyisoprene, or lambskin. The underwear 100 provides protection against sexually-transmitted diseases (STDs) or sexually-transmitted infections (STIs). It is also used as a barrier method of birth control (contraception) for preventing pregnancy by keeping the male wearer's sperm from reaching a female's eggs. The penis cover 108 collects ejaculation fluids and also prevents ejaculation fluids of the intercourse partner from touching the penis of the male user wearing the underwear 100. Further, as per the present embodiment, the penis cover 108 can be both lubricated or non-lubricated. Further, a flavoring agent and/or a spermicide in the form of a cream, gel, foam or film and can be coated on the penis cover 108.

In one potential embodiment, the penis cover 108 encloses, or at least partially encloses, the penis. The penis cover 108 can slip over the penile shaft and can be formed as a sleeve-like sack or pouch that includes an opening 110. The purpose of the opening 110 is to allow for easier insertion of the penis into the penis covering.

Figure 1B:
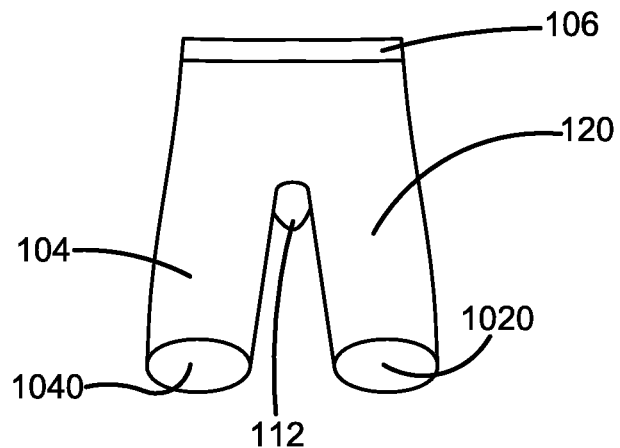
FIG. 1B illustrates a rear perspective view of one potential embodiment of the contraceptive underwear of the present invention designed for a male user in accordance with the disclosed architecture.

FIG. 1B illustrates a rear perspective view of one potential embodiment of the contraceptive underwear of the present invention designed for a male user in accordance with the disclosed architecture. The rear surface 120 of the underwear 100 conforms to the shape of the butt of the wearer, thereby providing a comfortable and watertight fit to the wearer. The leg elements 102, 104 cover the thighs, or upper thighs, of the male wearer.

In the preferred embodiment, the penis cover 108 acts as an integrated condom and can collapse when not in use. During use, the penis cover 108 extends away allowing the penis to move easily in desired directions. The penis cover 108 can include dots or ribs for increasing the pleasure of sexual intercourse. The integrated penis cover 108 eliminates the use of any additional condom and can fit over the penis in a manner similar to a conventional condom.

Figure 2:
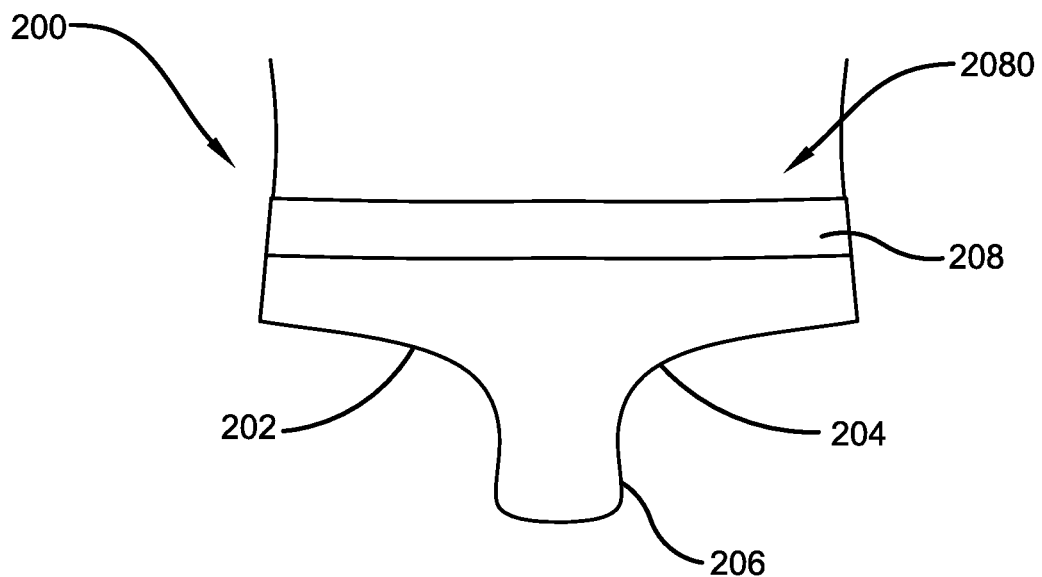
FIG. 2 illustrates a perspective view showing another embodiment of contraceptive underwear of the present invention for female users in accordance with the disclosed architecture.

FIG. 2 illustrates a perspective view showing another embodiment of contraceptive underwear of the present invention for female users in accordance with the disclosed architecture. The female contraceptive underwear 200 is especially designed for female users whose partners may not like to wear condoms during sexual intercourse. The female contraceptive underwear 200 is similar to a conventional female underwear and includes a right leg opening 202 and a left leg opening 204 for inserting legs therethrough. A crotch area 206 is configured to cover the crotch area of the female wearer and includes a waistband 208 defining a waist opening 2080 to receive and encircle the waist of the female user, but may also cover portions of the mid or upper thigh of the wearer. The female underwear 200 can be constructed of one or more materials such as latex, polyurethane, polyisoprene or lambskin. The underwear 200 can be flexible and can act as a barrier between skin-to-skin contact during intercourse while providing pleasure of sexual intercourse. The underwear 200 provides protection against sexually-transmitted diseases (STDs) and sexually transmitted infections (STIs). The underwear 200 can also be used as a barrier method of birth control (contraception) for preventing pregnancy by keeping the male wearer's sperm from reaching a female's eggs.

Figure 3:
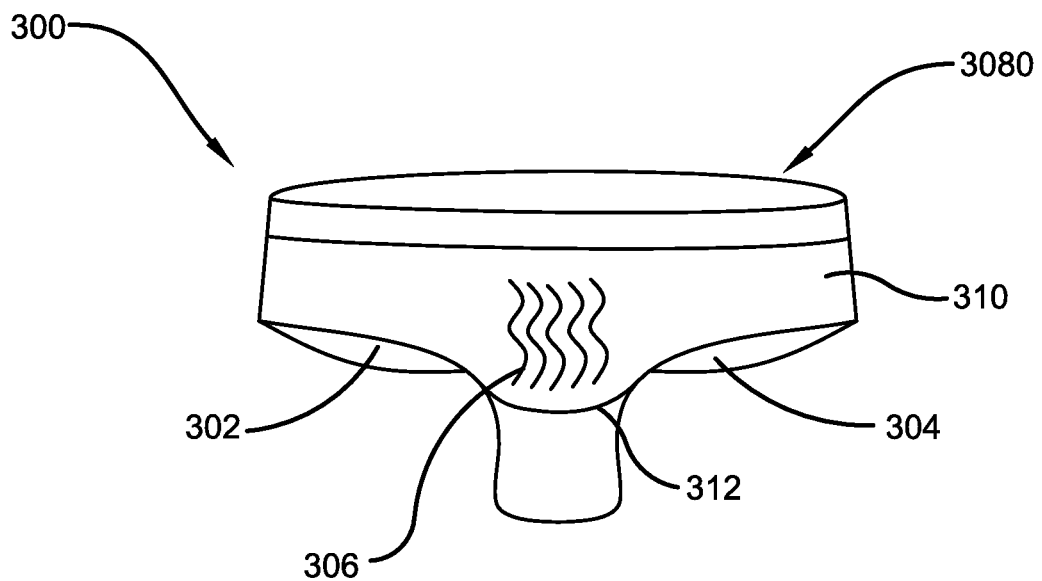
FIG. 3 illustrates a rear perspective view of another embodiment of contraceptive underwear of the present invention in the form of unisex short boxers for anal intercourse in accordance with the disclosed architecture.

FIG. 3 illustrates a rear perspective view of another embodiment of contraceptive underwear of the present invention in the form of unisex short boxers for anal intercourse in accordance with the disclosed architecture. In the present embodiment, the unisex contraceptive short boxer 300 is in the form of a trunk, and can be worn both by female and male users for safe and secure sexual intercourse. The contraceptive short boxer 300 is specially designed for anal intercourse. However, it can be effectively used for vaginal intercourse as well. More specifically, the contraceptive unisex short boxer 300 includes two leg openings 302, 304 and a waistband 308 defining a waist opening 3080 to create an opening to encircle the waist of a wearer. The contraceptive unisex short boxer 300 can be made of thin latex, or similar, and a rear surface 310 can include a relatively thinner latex layer 306 allowing effective and pleasurable anal intercourse.

The unisex contraceptive short boxer 300 can cover 90% of the wearer's buttock area and the crotch area 312 and can be used for having vaginal intercourse. Based on their preferences, any or both sexual partners can use the unisex contraceptive short boxer 300.

Figure 4:
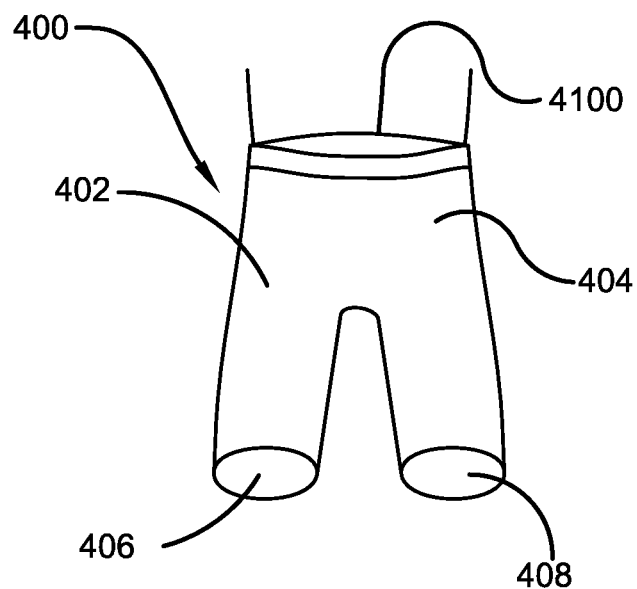
FIG. 4 illustrates a front perspective view showing a unisex long trunk embodiment of the contraceptive underwear of the present invention in accordance with the disclosed architecture.

FIG. 4 illustrates a front perspective view showing the unisex long trunk embodiment of the contraceptive underwear of the present invention in accordance with the disclosed architecture. In the present embodiment, the contraceptive underwear is in the form of a long unisex trunk 400 that can be worn by both males and females. The long unisex trunk 400 provides more coverage area and protection from skin-to-skin rubbing, contact and/or interaction during sexual intercourse. The long unisex trunk 400 includes a frontal region 402 to cover the front portion of a wearer and a rear region 404 to cover the buttocks of the wearer. The leg openings 406, 408 are used for inserting legs into them and a waistband 410 creates an opening 4100 to receive and encircle the waist and abdomen of the wearer. The long unisex trunk 400 can be made in any color, and can be constructed from one or more materials such as, but not limited to, a latex, plastic or lambskin.

The contraceptive undergarment of various embodiments of the present invention may be machine washable and reusable. In one variation, the contraceptive underwear can be disposable. Advantageously, the contraceptive undergarment of the present invention reduces fluid exchange during intense and creative sexual intercourse positions without the undergarment maneuvering off of the wearer.

It should be appreciated that that presently available condoms for both males and females allow only a limited protection from transmitting STDs. Further, the efficacy of the condoms can also be compromised. The undergarment of the present invention provides more coverage and protection from unwanted consequences during intercourse while not hindering sexual pleasure for both sexual partners. Because the contraceptive undergarment 100 covers more service area, there is less cleanup after intercourse or other use.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "contraceptive undergarment", "contraceptive underwear", "male underwear", "male contraceptive underwear", "underwear", "female contraceptive underwear", "unisex short boxers", "unisex contraceptive short boxer", and "unisex long trunk" are interchangeable and refer to the contraceptive undergarment 100 of the present invention.

Notwithstanding the forgoing, the contraceptive undergarment 100 of the present invention can be of any suitable size and configuration as is known in the art without affecting the overall concept of the invention, provided that it accomplishes the above-stated objectives. One of ordinary skill in the art will appreciate that the size, configuration and material of the contraceptive undergarment 100 as shown in the FIGS. are for illustrative purposes only, and that many other sizes and shapes of the contraceptive undergarment 100 are well within the scope of the present disclosure. Although the dimensions of the contraceptive undergarment 100 are important design parameters for user convenience, the contraceptive undergarment 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A contraceptive wearable undergarment comprising:
an undergarment having a frontal region, a rear region, a right leg opening, and a left leg opening for wearing said undergarment;
said frontal region includes a scrotum bag adapted to receive and stabilize scrotum of an individual;
said rear region includes a first material adapted to cover 90% of said individual's buttocks area and a second material adapted to cover a central area of the buttocks area, wherein said central area is an anal area;
said second material thinner than said first material;
said undergarment adapted to provide a barrier between skin-to-skin contact and bodily fluid exchange between individuals during intercourse;
said frontal region further includes an opening and a condom extending from said opening; and
wherein said opening adapted allow a penis to insert therethough and said condom adapted to receive said penis.

2. The contraceptive wearable undergarment of claim 1 wherein said undergarment is a short boxer.

3. The contraceptive wearable undergarment of claim 1, wherein said undergarment is a long trunk.

4. The contraceptive wearable undergarment of claim 1, wherein said undergarment is constructed of latex material.

5. The contraceptive wearable undergarment of claim 1, wherein said undergarment comprises a material selected from the group consisting of a polyurethane, a polyisoprene, and a lambskin.

6. The contraceptive wearable undergarment of claim 1 wherein said the condom includes a spermicide.

7. A contraceptive wearable undergarment comprising:
an undergarment having a frontal region, a rear region, a right leg opening, and a left leg opening for wearing said undergarment;
said frontal region includes a scrotum bag adapted to receive and stabilize scrotum of an individual;
said rear region includes a first material adapted to cover 90% of said individual's buttocks area and a second material adapted to cover a central area of the buttocks area, wherein said central area is an anal area;
said second material thinner than said first material;
said undergarment comprises a material selected from the group consisting of a latex, a polyurethane, a polyisoprene, and a lambskin;

said undergarment adapted to provide a barrier between skin-to-skin contact and bodily fluid exchange between individuals during intercourse;

said frontal region further includes an opening and a condom extending from said opening; and wherein said opening adapted allow a penis to insert therethough and said condom adapted to receive said penis.

* * * * *